(12) United States Patent
Schlarb et al.

(10) Patent No.: US 11,534,148 B2
(45) Date of Patent: Dec. 27, 2022

(54) BIOPSY DEVICE HAVING INTEGRATED VACUUM

(71) Applicant: C. R. Bard, Inc., Franklin Lakes, NJ (US)

(72) Inventors: Rory M. Schlarb, Paradise Valley, AZ (US); Chad C. Van Liere, Phoenix, AZ (US)

(73) Assignee: C. R. Bard, Inc., Franklin Lakes, NJ (US)

(*) Notice: Subject to any disclaimer, the term of this patent is extended or adjusted under 35 U.S.C. 154(b) by 629 days.

(21) Appl. No.: 16/570,097

(22) Filed: Sep. 13, 2019

(65) Prior Publication Data

US 2020/0000446 A1    Jan. 2, 2020

Related U.S. Application Data

(62) Division of application No. 15/034,339, filed as application No. PCT/US2013/068548 on Nov. 5, 2013, now Pat. No. 10,456,120.

(51) Int. Cl.
*A61B 10/02* (2006.01)

(52) U.S. Cl.
CPC ...... *A61B 10/0275* (2013.01); *A61B 10/0283* (2013.01); *A61B 2010/0208* (2013.01)

(58) Field of Classification Search
None
See application file for complete search history.

(56) References Cited

U.S. PATENT DOCUMENTS

| 737,293 A | 8/1903 | Summerfeldt |
| 1,585,934 A | 5/1926 | Muir |
| 1,663,761 A | 3/1928 | Johnson |

(Continued)

FOREIGN PATENT DOCUMENTS

| CN | 101011268 A | 8/2007 |
| CN | 101032420 A | 9/2007 |

(Continued)

OTHER PUBLICATIONS

MAXIM; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; pp. 1-14; Rev 1.

*Primary Examiner* — Matthew Kremer
(74) *Attorney, Agent, or Firm* — Dinsmore & Shohl LLP

(57) ABSTRACT

A biopsy device includes a housing body, and a cannula assembly that has a first elongate cannula and a second elongate cannula coaxial with the first elongate cannula. The second elongate cannula has a lumen and a side wall having a vacuum side port in fluid communication with the lumen. A vacuum source is positioned in the housing body. The vacuum source has a chamber side wall having a chamber vacuum port. A seal is interposed in sealing engagement between the chamber vacuum port and the second elongate cannula. A trigger slide assembly is coupled to the housing body, and coupled to the cannula assembly, and is configured to move the second elongate cannula to align the vacuum side port of the second elongate cannula with the chamber vacuum port of the vacuum source to supply vacuum from the vacuum source to the lumen of the second elongate cannula.

19 Claims, 8 Drawing Sheets

(56) References Cited

U.S. PATENT DOCUMENTS

| | | |
|---|---|---|
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |
| 3,800,783 A | 4/1974 | Jamshidi |
| 3,844,272 A | 10/1974 | Banko |
| 3,882,849 A | 5/1975 | Jamshidi |
| 3,889,682 A | 6/1975 | Denis et al. |
| 3,916,948 A | 11/1975 | Benjamin |
| 3,996,935 A | 12/1976 | Banko |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,792,327 A | 12/1988 | Swartz |
| 4,832,044 A | 5/1989 | Garg |
| 4,844,064 A | 7/1989 | Thimsen et al. |
| 4,844,087 A | 7/1989 | Garg |
| 4,850,354 A | 7/1989 | McGurk-Burleson et al. |
| 4,881,551 A | 11/1989 | Taylor |
| 4,893,635 A | 1/1990 | de Groot et al. |
| 4,907,598 A | 3/1990 | Bauer |
| 4,907,599 A | 3/1990 | Taylor |
| 4,924,878 A | 5/1990 | Nottke |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,121,751 A | 6/1992 | Panalletta |
| 5,125,413 A | 6/1992 | Baran |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,176,628 A | 1/1993 | Charles et al. |
| D333,183 S | 2/1993 | Cerola |
| 5,183,052 A | 2/1993 | Terwilliger |
| 5,197,484 A | 3/1993 | Kornberg et al. |
| 5,211,627 A | 5/1993 | William |
| 5,223,012 A | 6/1993 | Best et al. |
| D337,821 S | 7/1993 | Tan |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,254,117 A | 10/1993 | Rigby et al. |
| 5,282,476 A | 2/1994 | Terwilliger |
| 5,282,477 A | 2/1994 | Bauer |
| 5,290,253 A | 3/1994 | Kira |
| 5,305,762 A | 4/1994 | Acorn et al. |
| 5,324,306 A | 6/1994 | Makower et al. |
| 5,334,183 A | 8/1994 | Wuchinich |
| 5,335,671 A | 8/1994 | Clement |
| 5,335,672 A | 8/1994 | Bennett |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,602,449 A | 2/1997 | Krause et al. |
| 5,612,738 A | 3/1997 | Kim |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,871,699 A | 2/1999 | Ruggeri |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |

(56) References Cited

U.S. PATENT DOCUMENTS

| | | |
|---|---|---|
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 5,989,197 A | 11/1999 | Avaltroni |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,032,673 A | 3/2000 | Savage et al. |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,731 B2 | 3/2003 | Weiss et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,592,530 B1 | 7/2003 | Farhadi |
| D478,987 S | 8/2003 | Groenke et al. |
| 6,620,111 B2 | 9/2003 | Stephens et al. |
| 6,626,848 B2 | 9/2003 | Neuenfeldt |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,071 B2 | 2/2004 | Burbank et al. |
| 6,689,072 B2 | 2/2004 | Kaplan et al. |
| 6,695,786 B2 | 2/2004 | Wang et al. |
| 6,695,791 B2 | 2/2004 | Gonzalez |
| 6,702,832 B2 | 3/2004 | Ross et al. |
| 6,712,773 B1 | 3/2004 | Viola |
| 6,712,774 B2 | 3/2004 | Voegele et al. |
| 6,719,691 B2 | 4/2004 | Kritzman et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,758,848 B2 | 7/2004 | Burbank et al. |
| 6,764,495 B2 | 7/2004 | Lee et al. |
| 6,808,505 B2 | 10/2004 | Kadan |
| 6,832,990 B2 | 12/2004 | Kortenbach et al. |
| 6,840,950 B2 | 1/2005 | Stanford et al. |
| 6,849,080 B2 | 2/2005 | Lee et al. |
| 6,850,159 B1 | 2/2005 | Mudge |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,969,358 B2 | 11/2005 | Baltschun et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| 7,066,893 B2 | 6/2006 | Hibner et al. |
| D525,583 S | 7/2006 | Vu |
| 7,108,660 B2 | 9/2006 | Stephens et al. |
| 7,131,951 B2 | 11/2006 | Angel |
| 7,153,274 B2 | 12/2006 | Stephens et al. |
| 7,156,814 B1 | 1/2007 | Williamson, IV et al. |
| 7,156,815 B2 | 1/2007 | Leigh et al. |
| 7,169,114 B2 | 1/2007 | Krause |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,229,417 B2 | 6/2007 | Foerster et al. |
| 7,244,236 B2 | 7/2007 | Merkle |
| 7,252,641 B2 | 8/2007 | Thompson et al. |
| 7,276,032 B2 | 10/2007 | Hibner |
| 7,311,673 B2 | 12/2007 | Mueller, Jr. et al. |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,442,171 B2 | 10/2008 | Stephens et al. |
| 7,445,604 B2 | 11/2008 | Cash |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |

(56) References Cited

U.S. PATENT DOCUMENTS

| | | |
|---|---|---|
| 7,510,563 B2 | 3/2009 | Cesarini et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,556,622 B2 | 7/2009 | Mark et al. |
| 7,557,536 B2 | 7/2009 | Lobert et al. |
| 7,573,212 B2 | 8/2009 | Avis |
| 7,575,557 B2 | 8/2009 | Morton et al. |
| 7,588,176 B2 | 9/2009 | Timm et al. |
| 7,591,790 B2 | 9/2009 | Pflueger |
| 7,608,048 B2 | 10/2009 | Goldenberg |
| 7,611,475 B2 | 11/2009 | Spero et al. |
| 7,645,240 B2 | 1/2010 | Thompson et al. |
| 7,648,466 B2 | 1/2010 | Stephens et al. |
| 7,651,505 B2 | 1/2010 | Lubock et al. |
| 7,658,718 B2 | 2/2010 | Miller et al. |
| 7,662,109 B2 | 2/2010 | Hibner |
| 7,666,200 B2 | 2/2010 | Heisler |
| 7,670,299 B2 | 3/2010 | Beckman et al. |
| 7,693,567 B2 | 4/2010 | Tsonton et al. |
| 7,708,721 B2 | 5/2010 | Khaw |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,785,535 B2 | 8/2010 | Chen et al. |
| 7,794,411 B2 | 9/2010 | Ritchart et al. |
| 7,799,116 B2 | 9/2010 | Schwindt |
| 7,806,834 B2 | 10/2010 | Beckman et al. |
| 7,819,819 B2 | 10/2010 | Quick et al. |
| 7,828,746 B2 | 11/2010 | Teague |
| 7,828,747 B2 | 11/2010 | Heske et al. |
| 7,828,748 B2 | 11/2010 | Hibner |
| 7,837,630 B2 | 11/2010 | Nicoson et al. |
| 7,837,632 B2 | 11/2010 | Stephens et al. |
| 7,841,991 B2 | 11/2010 | Douglas et al. |
| 7,846,109 B2 | 12/2010 | Parihar et al. |
| 7,847,515 B2 | 12/2010 | Schroeck et al. |
| 7,854,706 B2 | 12/2010 | Hibner |
| 7,854,707 B2 | 12/2010 | Hibner et al. |
| 7,860,556 B2 | 12/2010 | Saadat |
| 7,862,517 B2 | 1/2011 | Tsonton et al. |
| 7,862,518 B2 | 1/2011 | Parihar |
| 7,867,173 B2 | 1/2011 | Hibner et al. |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,914,464 B2 | 3/2011 | Burdorff et al. |
| 7,959,580 B2 | 6/2011 | Mccullough et al. |
| 7,963,928 B2 | 6/2011 | Krause |
| 7,974,681 B2 | 7/2011 | Wallace et al. |
| 3,002,713 A1 | 8/2011 | Heske et al. |
| 7,987,766 B1 | 8/2011 | Price |
| 7,988,642 B2 | 8/2011 | Hardin et al. |
| 3,012,102 A1 | 9/2011 | McCullough et al. |
| 8,013,572 B2 | 9/2011 | Rodgers |
| 8,016,772 B2 | 9/2011 | Heske et al. |
| 8,016,844 B2 | 9/2011 | Privitera et al. |
| 8,016,855 B2 | 9/2011 | Whitman et al. |
| 8,034,003 B2 | 10/2011 | Pesce et al. |
| 8,042,689 B2 | 10/2011 | Fröjd et al. |
| 8,048,003 B2 | 11/2011 | Nicoson et al. |
| 8,052,614 B2 | 11/2011 | Heske et al. |
| 8,052,615 B2 | 11/2011 | Reuber et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,075,496 B2 | 12/2011 | Deck et al. |
| 8,075,568 B2 | 12/2011 | Selis |
| 8,083,671 B2 | 12/2011 | Boulais et al. |
| 8,083,687 B2 | 12/2011 | Parihar |
| 8,109,885 B2 | 2/2012 | Heske et al. |
| 8,109,886 B2 | 2/2012 | Miller et al. |
| 8,118,755 B2 | 2/2012 | Hibner et al. |
| 8,128,577 B2 | 3/2012 | Viola |
| 8,129,955 B2 | 3/2012 | White et al. |
| 8,152,738 B2 | 4/2012 | Li et al. |
| 8,157,744 B2 | 4/2012 | Jorgensen et al. |
| 8,162,850 B2 | 4/2012 | Parihar et al. |
| 8,162,851 B2 | 4/2012 | Heske et al. |
| D659,828 S | 5/2012 | Horning et al. |
| 8,167,818 B2 | 5/2012 | Miller |
| 8,172,771 B2 | 5/2012 | Miller et al. |
| 8,172,773 B2 | 5/2012 | Heske et al. |
| 8,177,728 B2 | 5/2012 | Hibner et al. |
| 8,177,729 B2 | 5/2012 | Hibner et al. |
| 8,183,825 B2 | 5/2012 | Sa |
| 8,187,204 B2 | 5/2012 | Miller et al. |
| 8,187,294 B2 | 5/2012 | Miller et al. |
| 8,190,238 B2 | 5/2012 | Moll et al. |
| 8,192,370 B2 | 6/2012 | Miller |
| 8,202,229 B2 | 6/2012 | Miller et al. |
| 8,206,316 B2 | 6/2012 | Hibner et al. |
| 8,206,409 B2 | 6/2012 | Privitera et al. |
| 8,241,331 B2 | 8/2012 | Arnin |
| 8,251,916 B2 | 8/2012 | Speeg et al. |
| 8,251,917 B2 | 8/2012 | Almazan |
| 8,261,847 B2 | 9/2012 | Ford et al. |
| 8,262,585 B2 | 9/2012 | Thompson et al. |
| 8,262,586 B2 | 9/2012 | Anderson et al. |
| 8,267,868 B2 | 9/2012 | Taylor et al. |
| 8,277,393 B2 | 10/2012 | Miller et al. |
| 8,282,573 B2 | 10/2012 | Shabaz et al. |
| 8,282,574 B2 | 10/2012 | Coonahan et al. |
| 8,283,890 B2 | 10/2012 | Videbaek |
| 8,287,465 B2 | 10/2012 | Hardin et al. |
| 8,287,466 B2 | 10/2012 | Weikel, Jr. et al. |
| 8,313,444 B2 | 11/2012 | Thompson et al. |
| 8,317,725 B2 | 11/2012 | Quick et al. |
| 8,343,069 B2 | 1/2013 | Uchiyama et al. |
| 8,357,103 B2 | 1/2013 | Mark et al. |
| 8,366,635 B2 | 2/2013 | Parihar et al. |
| 8,366,636 B2 | 2/2013 | Videbaek |
| 8,430,824 B2 | 4/2013 | Videbaek et al. |
| 8,430,825 B2 | 4/2013 | Mark |
| 8,430,827 B2 | 4/2013 | Nicoson et al. |
| 8,480,595 B2 | 7/2013 | Speeg et al. |
| 8,485,987 B2 | 7/2013 | Videbaek et al. |
| 8,485,989 B2 | 7/2013 | Videbaek |
| 8,491,496 B2 | 7/2013 | Hibner |
| 8,506,504 B2 | 8/2013 | Field et al. |
| 8,529,468 B2 | 9/2013 | Hoffa et al. |
| 8,529,593 B2 | 9/2013 | Berberich |
| 8,540,646 B2 | 9/2013 | Mendez-Coll |
| 8,574,167 B2 | 11/2013 | Smith et al. |
| 8,591,435 B2 | 11/2013 | Ritchart et al. |
| 8,594,339 B2 | 11/2013 | Dufresne et al. |
| 8,597,205 B2 | 12/2013 | Seiger et al. |
| 8,597,206 B2 | 12/2013 | Videback |
| 8,600,299 B2 | 12/2013 | Randall et al. |
| 8,672,860 B2 | 3/2014 | Moore et al. |
| 8,690,793 B2 | 4/2014 | Ranpura et al. |
| 8,696,650 B2 | 4/2014 | Quick et al. |
| 8,702,621 B2 | 4/2014 | Mccullough et al. |
| 8,702,622 B2 | 4/2014 | McCullough et al. |
| 8,702,623 B2 | 4/2014 | Parihar et al. |
| 8,708,928 B2 | 4/2014 | Videbaek |
| 8,708,929 B2 | 4/2014 | Videbaek |
| 8,708,930 B2 | 4/2014 | Videbaek |
| 8,721,563 B2 | 5/2014 | Taylor et al. |
| 8,728,003 B2 | 5/2014 | Taylor et al. |
| 8,728,004 B2 | 5/2014 | Heske et al. |
| 8,764,664 B2 | 7/2014 | Callahan et al. |
| 8,771,200 B2 | 7/2014 | Thompson et al. |
| 8,795,195 B2 | 8/2014 | Daw et al. |
| 8,808,197 B2 | 8/2014 | Videbaek et al. |
| 8,858,463 B2 | 10/2014 | Seiger et al. |
| 8,864,680 B2 | 10/2014 | Videbæk et al. |

(56) References Cited

U.S. PATENT DOCUMENTS

| | | |
|---|---|---|
| 8,926,527 B2 | 1/2015 | Jørgensen et al. |
| 8,932,233 B2 | 1/2015 | Haberstich et al. |
| 8,951,208 B2 | 2/2015 | Almazan |
| 8,951,209 B2 | 2/2015 | Heske et al. |
| 8,956,306 B2 | 2/2015 | Hibner |
| 8,961,430 B2 | 2/2015 | Coonahan et al. |
| 8,992,440 B2 | 3/2015 | Reuber et al. |
| 9,023,292 B2 | 5/2015 | Rostaing et al. |
| 9,044,227 B2 | 6/2015 | Shelton, IV et al. |
| 9,072,502 B2 | 7/2015 | Heske et al. |
| 9,095,326 B2 | 8/2015 | Ritchie et al. |
| 9,161,743 B2 | 10/2015 | Mccullough et al. |
| 9,162,884 B2 | 10/2015 | Hoon et al. |
| 9,173,641 B2 | 11/2015 | Chudzik et al. |
| 9,220,573 B2 | 12/2015 | Kendrick et al. |
| 9,282,949 B2 | 3/2016 | Videbaek |
| 9,332,972 B2 | 5/2016 | Boutaghou et al. |
| 9,345,457 B2 | 5/2016 | Speeg et al. |
| 9,345,458 B2 | 5/2016 | Videbaek et al. |
| 9,421,002 B2 | 8/2016 | Heske et al. |
| 9,439,631 B2 | 9/2016 | Heske et al. |
| 9,439,632 B2 | 9/2016 | Almazan |
| 9,445,790 B2 | 9/2016 | Zinn et al. |
| 9,451,968 B2 | 9/2016 | Miller et al. |
| 9,456,809 B2 | 10/2016 | Jorgensen et al. |
| 9,566,045 B2 | 2/2017 | Videbaek et al. |
| 9,638,770 B2 | 5/2017 | Dietz et al. |
| 9,655,599 B2 | 5/2017 | Chudzik et al. |
| 2001/0007925 A1 | 7/2001 | Ritchart et al. |
| 2001/0012919 A1 | 8/2001 | Terwilliger |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1 | 1/2002 | Tanaka et al. |
| 2002/0067151 A1 | 6/2002 | Tanishita |
| 2002/0068878 A1 | 6/2002 | Jasonni et al. |
| 2002/0107043 A1 | 8/2002 | Adamson et al. |
| 2002/0120212 A1 | 8/2002 | Ritchart et al. |
| 2003/0093103 A1 | 5/2003 | Malackowski et al. |
| 2003/0163142 A1 | 8/2003 | Paltieli et al. |
| 2004/0030367 A1 | 2/2004 | Yamaki et al. |
| 2004/0092992 A1 | 5/2004 | Adams et al. |
| 2004/0158172 A1 | 8/2004 | Hancock |
| 2004/0162505 A1 | 8/2004 | Kaplan et al. |
| 2004/0220495 A1 | 11/2004 | Cahir et al. |
| 2004/0230188 A1 | 11/2004 | Cioanta et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0049521 A1 | 3/2005 | Miller et al. |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0177117 A1 | 8/2005 | Crocker et al. |
| 2005/0193451 A1 | 9/2005 | Quistgaard et al. |
| 2005/0209530 A1 | 9/2005 | Pflueger |
| 2005/0275378 A1 | 12/2005 | Canino et al. |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0116603 A1 | 6/2006 | Shibazaki et al. |
| 2006/0122535 A1 | 6/2006 | Daum |
| 2006/0178666 A1 | 8/2006 | Cosman et al. |
| 2006/0184063 A1 | 8/2006 | Miller |
| 2006/0241515 A1 | 10/2006 | Jones et al. |
| 2007/0016101 A1 | 1/2007 | Feldman et al. |
| 2007/0055173 A1 | 3/2007 | DeLonzor et al. |
| 2007/0090788 A1 | 4/2007 | Hansford et al. |
| 2007/0106176 A1 | 5/2007 | Mark et al. |
| 2007/0161925 A1 | 7/2007 | Quick et al. |
| 2007/0167943 A1 | 7/2007 | Janssen et al. |
| 2007/0213590 A1 | 9/2007 | Squicciarini |
| 2007/0213632 A1 | 9/2007 | Okazaki et al. |
| 2007/0270710 A1 | 11/2007 | Frass et al. |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0030170 A1 | 2/2008 | Dacquay et al. |
| 2008/0064925 A1 | 3/2008 | Gill et al. |
| 2008/0103411 A1 | 5/2008 | Van Bladel et al. |
| 2008/0125634 A1 | 5/2008 | Ryan et al. |
| 2008/0146965 A1 | 6/2008 | Privitera et al. |
| 2008/0161720 A1 | 7/2008 | Nicoson et al. |
| 2008/0200835 A1 | 8/2008 | Monson et al. |
| 2008/0208194 A1 | 8/2008 | Bickenbach |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0228104 A1 | 9/2008 | Uber et al. |
| 2009/0030442 A1 | 1/2009 | Potter et al. |
| 2009/0062624 A1 | 3/2009 | Neville |
| 2009/0082695 A1 | 3/2009 | Whitehead |
| 2009/0087249 A1 | 4/2009 | Flagle et al. |
| 2009/0146609 A1 | 6/2009 | Santos |
| 2009/0204022 A1 | 8/2009 | Schwindt |
| 2009/0281453 A1 | 11/2009 | Tsonton et al. |
| 2010/0030020 A1 | 2/2010 | Sanders et al. |
| 2010/0063416 A1 | 3/2010 | Cicenas et al. |
| 2010/0152610 A1 | 6/2010 | Parihar et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0224577 A1 | 9/2011 | Park |
| 2012/0080332 A1 | 4/2012 | Shelton, IV et al. |
| 2012/0191009 A1 | 7/2012 | Hoon et al. |
| 2012/0253225 A1 | 10/2012 | Boutaghou et al. |
| 2012/0265096 A1 | 10/2012 | Mendez-Coll |
| 2013/0023789 A1 | 1/2013 | Anderson et al. |
| 2013/0165815 A1 | 6/2013 | Zinn et al. |
| 2013/0289441 A1 | 10/2013 | Videbaek et al. |
| 2014/0358032 A1 | 12/2014 | Videbaek et al. |
| 2014/0371585 A1 | 12/2014 | Thompson et al. |
| 2015/0018712 A1 | 1/2015 | Seiger et al. |
| 2015/0190124 A1 | 7/2015 | Mccullough et al. |
| 2015/0223787 A1 | 8/2015 | Coonahan et al. |
| 2015/0238174 A1 | 8/2015 | Reuber et al. |
| 2016/0256138 A1 | 9/2016 | Videbaek et al. |
| 2016/0262733 A1 | 9/2016 | Schlarb et al. |
| 2016/0317133 A1 | 11/2016 | Orts et al. |
| 2016/0367229 A1 | 12/2016 | Jorgensen et al. |
| 2016/0367230 A1 | 12/2016 | Almazan |
| 2016/0374650 A1 | 12/2016 | Heske et al. |
| 2017/0042517 A1 | 2/2017 | Heske et al. |
| 2017/0181732 A1 | 6/2017 | Videbaek et al. |

FOREIGN PATENT DOCUMENTS

| | | |
|---|---|---|
| DE | 3924291 A1 | 1/1991 |
| DE | 4041614 C1 | 10/1992 |
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1642535 A1 | 4/2006 |
| EP | 1665989 A2 | 6/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |

(56) References Cited

FOREIGN PATENT DOCUMENTS

| | | | |
|---|---|---|---|
| GB | 2018601 A | 10/1979 | |
| JP | 1-126957 A | 9/1987 | |
| JP | H10508504 A | 8/1998 | |
| JP | 2005530554 A | 10/2005 | |
| JP | 2006509545 A | 3/2006 | |
| JP | 2006528907 A | 12/2006 | |
| JP | 2007502159 A | 2/2007 | |
| WO | 9508945 A2 | 4/1995 | |
| WO | 9628097 A1 | 9/1996 | |
| WO | 9734531 A1 | 9/1997 | |
| WO | 9825522 A1 | 6/1998 | |
| WO | 9831285 A1 | 7/1998 | |
| WO | 9835615 A1 | 8/1998 | |
| WO | 9846290 A1 | 10/1998 | |
| WO | 9933501 A1 | 7/1999 | |
| WO | 0004832 A1 | 2/2000 | |
| WO | 0030546 A1 | 6/2000 | |
| WO | 0059378 A2 | 10/2000 | |
| WO | 0172230 A1 | 10/2001 | |
| WO | 0222023 A1 | 3/2002 | |
| WO | 0232318 A1 | 4/2002 | |
| WO | 02069808 A2 | 9/2002 | |
| WO | WO-2004052212 A1 * | 6/2004 | ......... A61B 10/0275 |
| WO | 2005013830 A1 | 2/2005 | |
| WO | 2006015302 A1 | 2/2006 | |
| WO | 2007047128 A1 | 4/2007 | |
| WO | 2007095330 A2 | 8/2007 | |
| WO | 2007112751 A2 | 10/2007 | |
| WO | 2008021687 A1 | 2/2008 | |
| WO | 2008040812 A1 | 4/2008 | |
| WO | 2008131362 A2 | 10/2008 | |
| WO | 2010107424 A1 | 9/2010 | |
| WO | 2010120294 A1 | 10/2010 | |
| WO | 2011019343 A1 | 2/2011 | |
| WO | 2013158072 A1 | 10/2013 | |
| WO | 2014153410 A1 | 9/2014 | |

\* cited by examiner

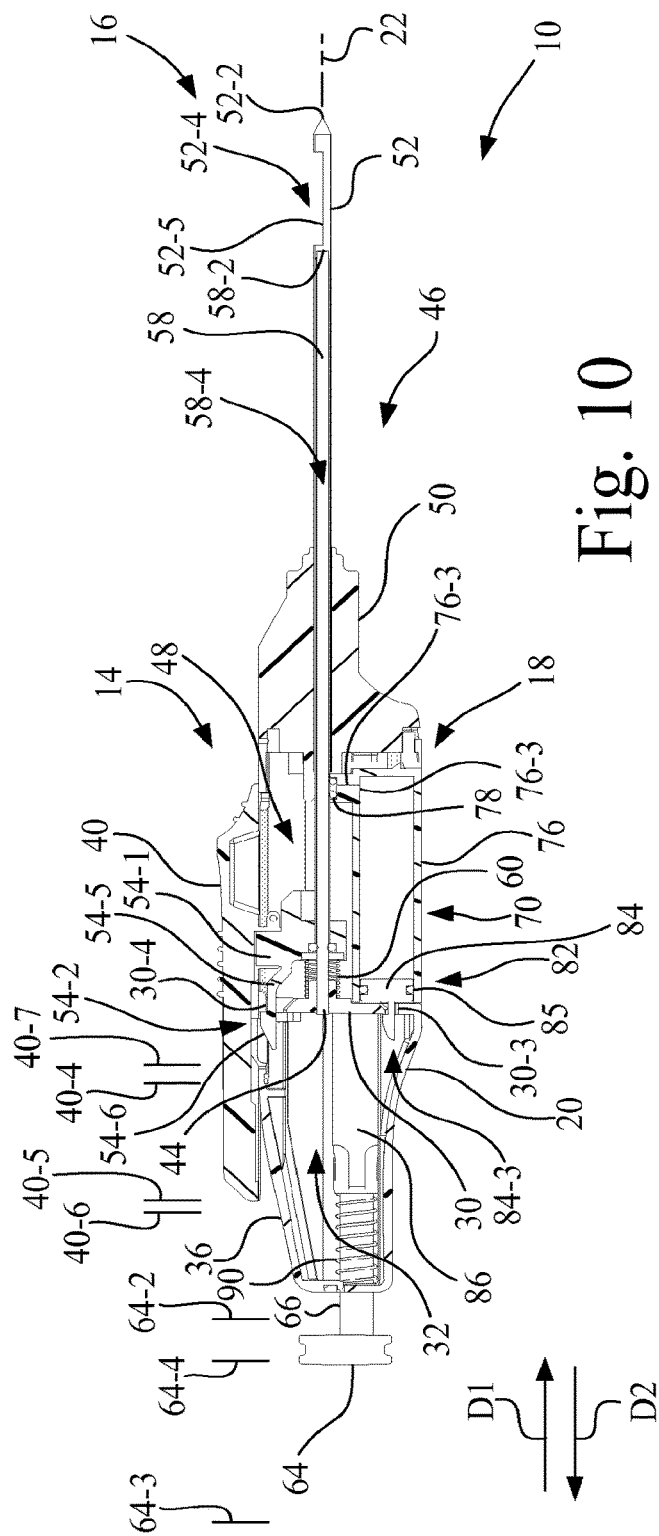
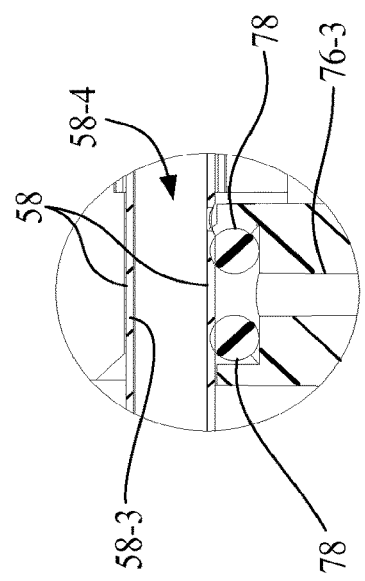
Fig. 10
Fig. 11

BIOPSY DEVICE HAVING INTEGRATED VACUUM

CROSS-REFERENCE TO RELATED APPLICATIONS

This application is a divisional of U.S. patent application Ser. No. 15/034,339, filed May 4, 2016, which is a U.S. national phase of International Application No. PCT/US2013/068548, filed Nov. 5, 2013.

BACKGROUND OF THE INVENTION

1. Field of the Invention

The present invention relates to biopsy devices, and, more particularly, to a handheld single insertion single sample (SISS) biopsy device having integrated vacuum.

2. Description of the Related Art

Biopsy devices typically include a power source and a sample retrieval mechanism. The sample retrieval mechanism may be in the form of a biopsy probe assembly configured with a sample retrieval opening for receiving tissue samples from the patient. Some practitioners that perform biopsy procedures prefer a self-contained handheld biopsy device over that of a large console system. There are essentially two types of self-contained handheld biopsy devices: the partially disposable biopsy device and the fully disposable biopsy device.

A typical partially disposable biopsy device has a reusable handheld driver to which a disposable probe is releasably attached. The reusable handheld driver is typically battery powered, and includes electrical motor drives and an onboard vacuum pump to aid in sample acquisition and/or retrieval. Often, such biopsy devices are configured for single insertion multiple sample (SIMS) procedures. The disposable probe is used on a single patient, and then discarded, while the handheld driver is retained for reuse.

A typical fully disposable biopsy device has one or more mechanical drives, such as spring/latch arrangements, which permit the biopsy device to be manually cocked and fired for tissue sample acquisition. Such simple biopsy devices often are configured to acquire a single sample per insertion. Also, many of the fully disposable biopsy devices do not have vacuum to assist in sample acquisition. While some attempts have been made to include a vacuum assist feature in a fully disposable biopsy device, the vacuum produced typically is not sufficient to approach the performance of that of a partially disposable biopsy device as described above. Also, in a typical fully disposable biopsy device having vacuum assist, such vacuum is generated simultaneously with movement of the cutting cannula to sever the tissue sample, and thus the vacuum may be of limited value in acquiring the tissue sample.

What is needed in the art is a biopsy device that may be fully disposable, while having efficient vacuum application to aid in sample acquisition, and which is configured to be easy to use.

SUMMARY OF THE INVENTION

The present invention provides a biopsy device that is fully disposable, while having efficient vacuum application to aid in sample acquisition, and which is configured to be easy to use.

The invention, in one form, is directed to a biopsy device having a housing body, a cannula assembly, a vacuum source and a trigger slide assembly. The housing body defines a longitudinal axis. The cannula assembly has a first elongate cannula having a first side wall configured to define a first lumen and an elongate side opening that extends through the first side wall. A second elongate cannula is coaxial with the first elongate cannula. The second elongate cannula has a second side wall configured to define a second lumen and a cutting edge. The second side wall has a vacuum side port in fluid communication with the second lumen. A vacuum source is positioned in the housing body. The vacuum source has a chamber side wall having a chamber vacuum port. A seal is interposed in sealing engagement between the chamber vacuum port and the second elongate cannula. A trigger slide assembly is coupled to the housing body, and is coupled to the cannula assembly. The trigger slide assembly is configured to move the second elongate cannula to align the vacuum side port of the second elongate cannula with the chamber vacuum port of the vacuum source to supply vacuum from the vacuum source to the second lumen of the second elongate cannula.

The invention, in another form, is directed to a biopsy device that includes a housing body defining a longitudinal axis. A first cannula assembly has a first elongate cannula that extends along the longitudinal axis. The first elongate cannula has a first side wall configured to define a first lumen and has an elongate side opening that extends through the first side wall. A second cannula assembly includes a second cannula body coupled to a second elongate cannula that is slidably received in the first lumen of the first elongate cannula. The second cannula body has a drive tab and a proximal latch mechanism configured to releasably latch the second elongate cannula in a retracted position. The second elongate cannula has a second side wall having a second lumen, and has a vacuum side port that extends through the second side wall and is in fluid communication with the second lumen. A cannula drive spring is configured to compress when the proximal latch mechanism is moved to the retracted position and configured to decompress to propel the second cannula assembly in a distal direction when the proximal latch mechanism is released from the retracted position. A vacuum source is positioned in the housing body. The vacuum source is configured to store a vacuum. The vacuum source includes a chamber side wall defining a volume. The chamber side wall has a chamber vacuum port. A vacuum seal is interposed in sealing engagement between the chamber vacuum port and the second elongate cannula. A trigger slide assembly has a slider body coupled to the housing body and coupled to the drive tab of the second cannula body. The trigger slide assembly is configured such that: a first proximal movement of the slider body in a proximal direction retracts the second cannula assembly a first distance to latch the proximal latch mechanism of the second cannula assembly in the retracted position and compress the cannula drive spring; a second proximal movement of the slider body in the proximal direction retracts the second cannula assembly a second distance cumulative with the first distance to radially align the vacuum side port of the second elongate cannula with the chamber vacuum port of the vacuum source to supply vacuum from the vacuum source to the second lumen of the second elongate cannula; and a third movement of the slider body releases the proximal latch mechanism such that the cannula drive spring decompresses to propel the second elongate cannula of the second cannula assembly in a distal direction.

The invention in another form is directed to a biopsy device. The biopsy device includes a housing body defining a longitudinal axis. A cannula assembly has an actuator body and an elongate cannula affixed to the actuator body. The elongate cannula has a side wall defining a lumen, and has a vacuum side port that extends through the side wall and is in fluid communication with the lumen. The actuator body has a drive tab and a proximal latch mechanism. The proximal latch mechanism is configured to selectively engage the housing body to releasably latch the cannula assembly in a retracted position. A cannula drive spring is coupled between the housing body and the actuator body. The cannula drive spring is configured to be compressed when the proximal latch mechanism is moved to the retracted position and configured to decompress to propel the elongate cannula in a distal direction when the proximal latch mechanism is released from the retracted position. A vacuum source is coupled to the housing body and is configured to store a vacuum. The vacuum source includes a vacuum chamber housing having a chamber open end, a chamber end wall, a chamber side wall extending between the chamber open end and the chamber end wall, and a chamber vacuum port. The chamber side wall has a perimeter defining a U-shaped area in cross-section that extends longitudinally between the chamber open end and the chamber end wall to define a U-shaped volume. A trigger slide assembly has a slider body operatively coupled to the drive tab of the cannula assembly and to the vacuum source.

The invention in another form is directed to a biopsy device that includes a housing body and a cannula assembly having an actuator body and an elongate cannula affixed to the actuator body. The elongate cannula has a side wall defining a lumen, and has a vacuum side port that extends through the side wall and in fluid communication with the lumen. The actuator body has a drive tab and a proximal latch mechanism. The proximal latch mechanism is configured to selectively engage the housing body to releasably latch the cannula assembly in a retracted position. A cannula drive spring is coupled between the housing body and the actuator body. The cannula drive spring is configured to be compressed when the proximal latch mechanism is moved to the retracted position and is configured to decompress to propel the elongate cannula in a distal direction when the proximal latch mechanism is released from the retracted position. A vacuum source is coupled to the housing body and is configured to store a vacuum. The vacuum source includes a vacuum chamber housing having a chamber side wall having a chamber vacuum port. A trigger slide assembly has a slider body slidably coupled to the housing body, and operatively coupled to the drive tab of the actuator body of the cannula assembly. The trigger slide assembly is configured such that: a first proximal movement of the slider body retracts the cannula assembly a first distance to latch the cannula assembly in the retracted position and to compress the cannula drive spring; a second proximal movement of the slider body retracts the cannula assembly a second distance cumulative with the first distance to align the vacuum side port of the elongate cannula with the chamber vacuum port of the vacuum source to supply vacuum from the vacuum source to the second lumen of the elongate cannula; and a third movement of the slider body in a distal direction releases the proximal latch mechanism such that the cannula drive spring decompresses to propel the cannula assembly in the distal direction.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 10 is a section view corresponding to the section of FIG. 7, showing the slider body of the trigger slide assembly in a first retracted primed position, and the inner cannula assembly in the primed (cocked) position;

FIG. 11 is an enlarged view of a portion of the section view of FIG. 10 showing the vacuum source with the chamber vacuum port closed by the cutting cannula side wall;

Corresponding reference characters indicate corresponding parts throughout the several views. The exemplification set out herein illustrates an embodiment of the invention and such exemplification is not to be construed as limiting the scope of the invention in any manner.

DETAILED DESCRIPTION OF THE INVENTION

Figure 1:
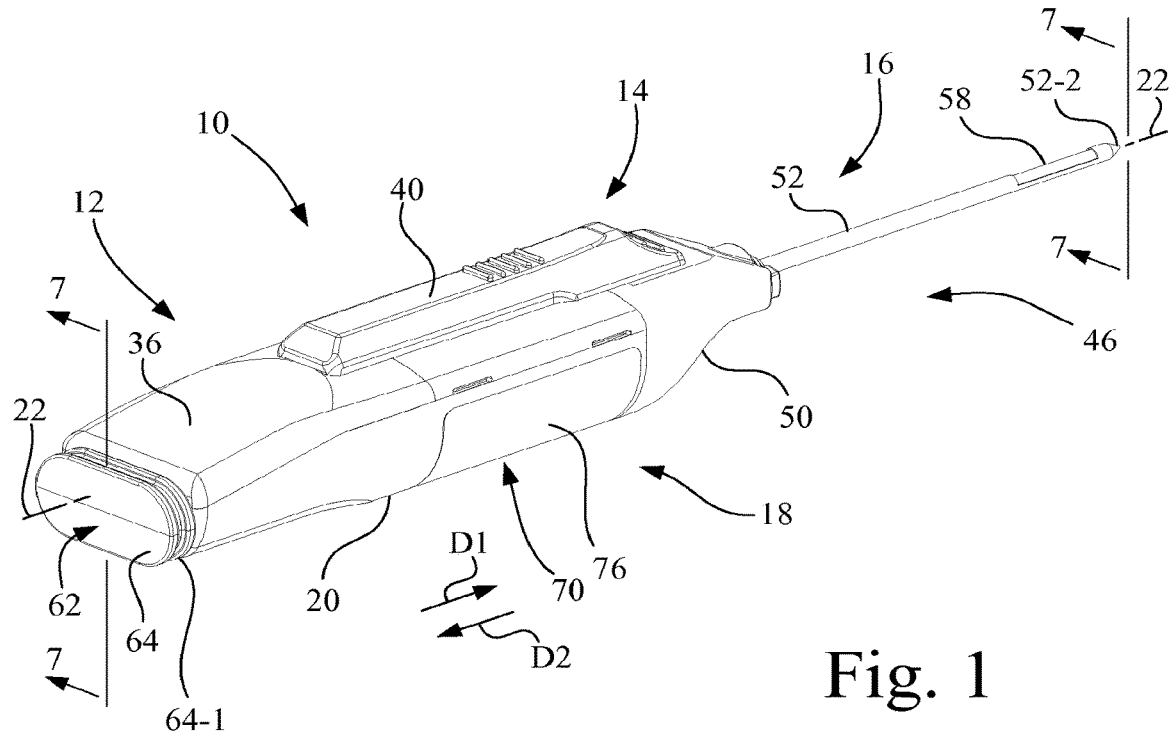
FIG. 1 is a perspective view of a biopsy device in accordance with an embodiment of the present invention.

Referring now to the drawings, and more particularly to FIGS. 1-7, there is shown a biopsy device 10 in accordance with an embodiment of the present invention. Biopsy device 10 is configured as a single insertion single sample (SISS) biopsy device, which is fully disposable.

Figure 2:
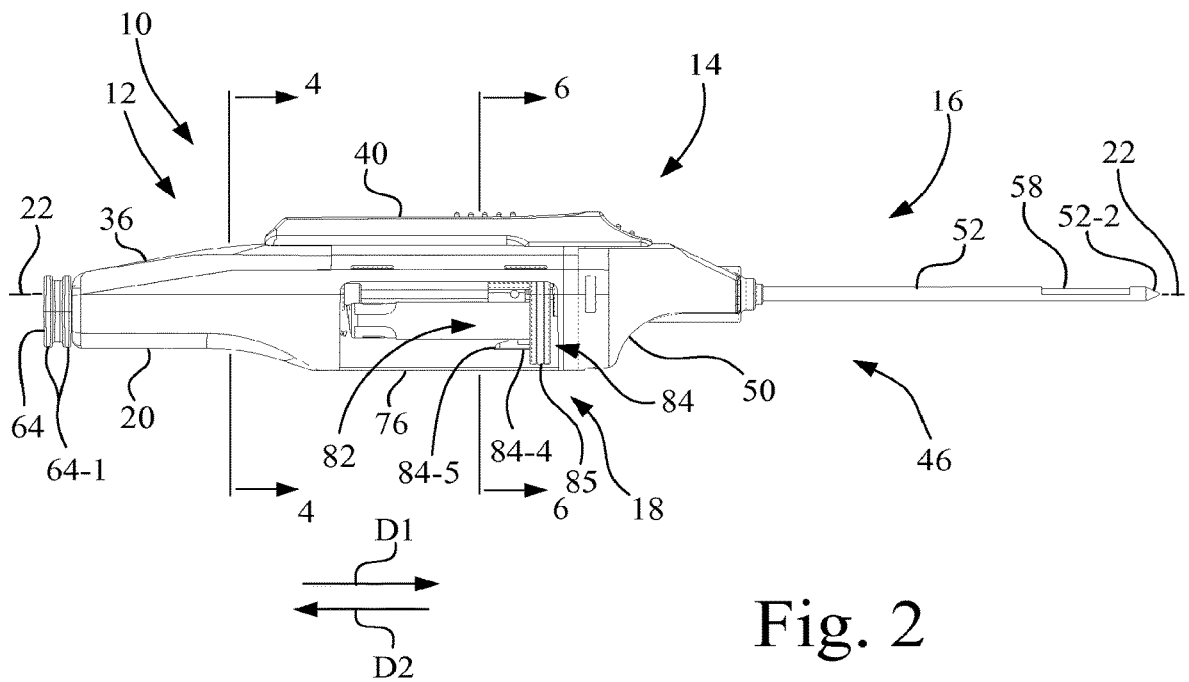
FIG. 2 is a side view of the biopsy device of FIG. 1.
Figure 3:
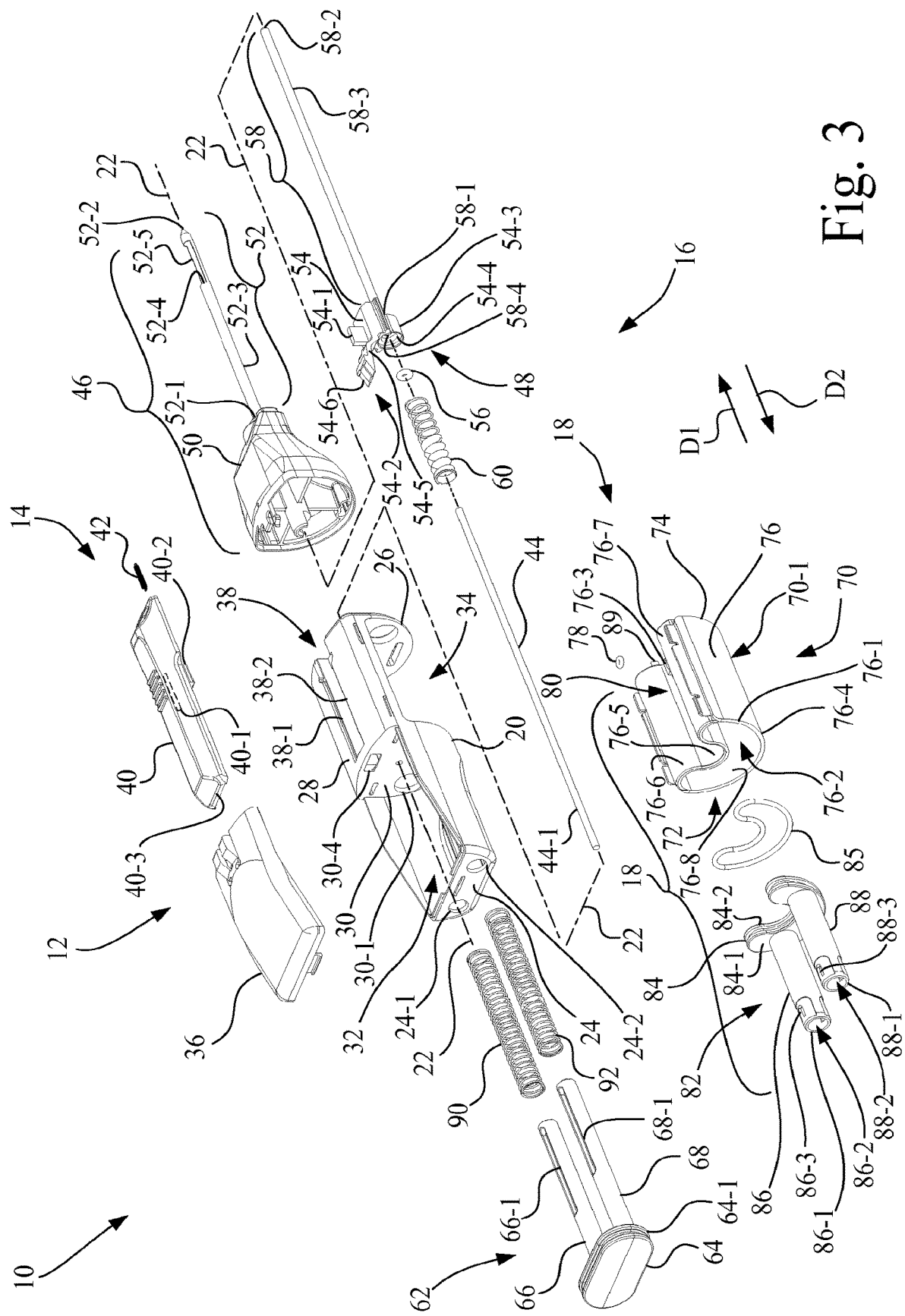
FIG. 3 is an exploded view of the biopsy device of FIG. 1.

As shown in FIGS. 1-3, biopsy device 10 generally includes a housing 12, a trigger slide assembly 14, a cannula assembly 16, and a vacuum source 18. In describing biopsy device 10, for convenience, reference will be made to distal direction D1 and proximal direction D2.

Housing 12 includes a housing body 20 that defines a longitudinal axis 22. Housing body 20 has a proximal end wall 24, a distal end wall 26, an upper surface 28, and an interior wall 30. Interior wall 30 is located between proximal end wall 24 and distal end wall 26. Interior wall 30 separates the housing body 20 into a proximal chamber 32 and a distal chamber 34. A chamber cover 36 is removably attached to housing body 20 to enclose proximal chamber 32.

Proximal end wall 24 has a pair of handle link openings 24-1, 24-2.

Figure 4:
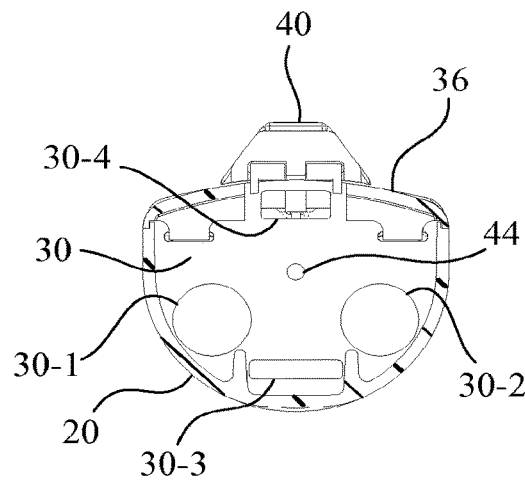
FIG. 4 is a section view of the biopsy device of FIG. 2, taken along plane 4-4.
Figure 5:
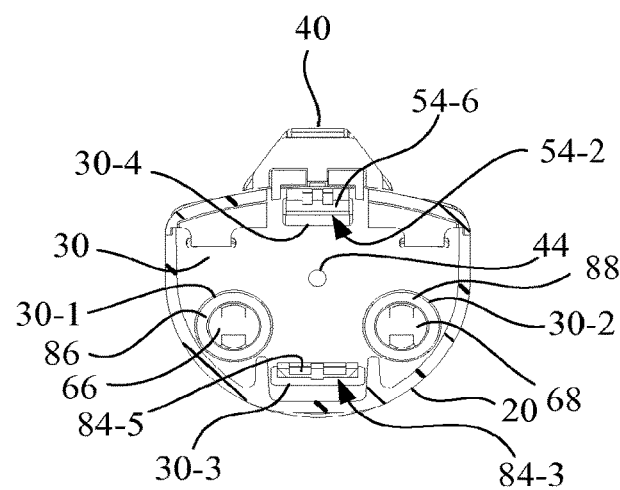
FIG. 5 is a section view corresponding to the section view of FIG. 4, showing the latch mechanisms of the inner cannula assembly and the vacuum source in their respective latched (primed) positions.

Referring also to FIGS. 4 and 5, interior wall 30 has two piston link openings 30-1, 30-2, a piston latch opening 30-3, and a cannula latch opening 30-4.

As best shown in FIG. 3, upper surface 28 of the housing body 20 has an elongate slide slot 38 that defines a first slide slot edge 38-1 and a second slide slot edge 38-2. Second slide slot edge 38-2 is spaced apart from the first slide slot edge 38-1 in a direction perpendicular to the longitudinal axis 22.

Trigger slide assembly 14 is coupled to housing body 20 at elongate slide slot 38. Trigger slide assembly 14 includes a slider body 40 having a pair of opposed channels 40-1, 40-2 configured to respectively receive the first slide slot edge 38-1 and the second slide slot edge 38-2 of the elongate slide slot 38 of the housing body 20. Trigger slide assembly 14 is biased in the distal direction D1 by a biasing spring 42.

Referring also to FIGS. 7-10, 12 and 14, and using a proximal end 40-3 of slider body 40 as a point of reference, slider body 40 has four positions, namely: a home position 40-4, a first proximal position 40-5, a second proximal position 40-6, and a distal-most position 40-7. The four positions of slider body 40 will be described in more detail below.

As best shown in FIG. 3, cannula assembly 16 includes a cannula support rod 44, an outer cannula assembly 46, and an inner cannula assembly 48.

Cannula support rod 44 is disposed in housing body 20 on and co-extensive with the longitudinal axis 22. Cannula support rod 44 has a proximal end 44-1 connected to the interior wall 30 of the housing body 20. Cannula support rod 44 provides radial support along longitudinal axis 22 for the stationary outer cannula assembly 46 as well as the movable inner cannula assembly 48.

Outer cannula assembly 46 has an end cap body 50 and an elongate outer cannula 52 that extends along the longitudinal axis 22. End cap body 50 is connected to housing body 20 at distal end wall 26 of the housing body 20. As such, outer cannula 52 is stationary relative to housing body 20. Outer cannula 52 is coaxial with cannula support rod 44, and is received over a portion of cannula support rod 44.

Outer cannula 52 has an end 52-1, a penetrating tip 52-2, and a side wall 52-3 that extends between the end 52-1 and penetrating tip 52-2. The end 52-1 is affixed to end cap body 50. Side wall 52-3 is configured to define a lumen 52-4 and has an elongate side opening 52-5 that extends through side wall 52-3. Elongate side opening 52-5 is thus in fluid communication with the lumen 52-4. Elongate side opening 52-5 is configured to receive a tissue sample during a biopsy procedure.

Inner cannula assembly 48 includes an actuator body 54, a cannula support rod seal 56, and an elongate cutting cannula 58.

Figure 7:
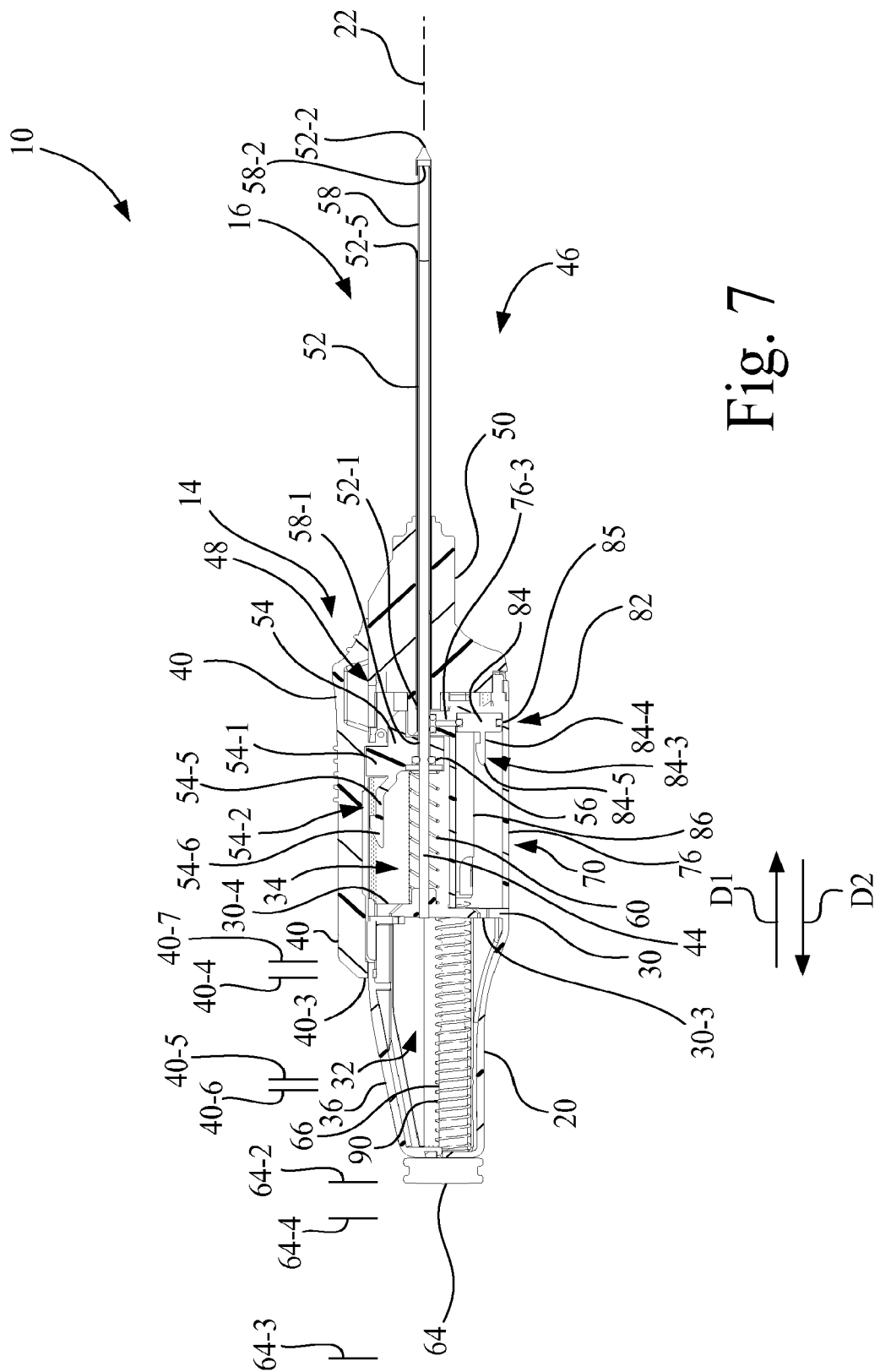
FIG. 7 is a section view of the biopsy device of FIGS. 1 and 2, taken along the plane 7-7 of FIG. 1, and showing the vacuum source, the inner cannula assembly, the vacuum prime handle mechanism, and the slider body of the trigger slide assembly in their respective home positions.

Referring also to FIG. 7 in conjunction with FIG. 3, actuator body 54 has a drive tab 54-1, a proximal latch mechanism 54-2, a cannula mount 54-3 and proximal axial bore 54-4. Drive tab 54-1 is configured to engage slider body 40 of trigger slide assembly 14 for longitudinal movement therewith, e.g., in the proximal direction D2.

Referring also to FIG. 10, together, proximal latch mechanism 54-2 of actuator body 54 and cannula latch opening 30-4 of interior wall 30 of housing body 20 form a snap featured detent. Proximal latch mechanism 54-2 is configured to pass through the cannula latch opening 30-4 of interior wall 30 of housing body 20, to thereby releasably latch the elongate cutting cannula 58 in a retracted (primed, or sometimes referred to as cocked) position. More particularly, proximal latch mechanism 54-2 is in the form of a cantilever arm 54-5 having at its free end a latch head 54-6 configured to catch a portion of interior wall 30 (see also FIG. 5) adjacent cannula latch opening 30-4 in proximal chamber 32 to releasably latch the elongate cutting cannula 58 in the retracted (primed, or cocked) position.

Cutting cannula 58 is coaxial with cannula support rod 44 and outer cannula 52. More particularly, in the present embodiment, cutting cannula 58 is radially interposed between cannula support rod 44 and outer cannula 52, with cutting cannula 58 being slidably received in the lumen 52-4 of outer cannula 52 and slidably receiving cannula support rod 44.

As best shown in FIG. 3, cutting cannula 58 has an end portion 58-1, a distal cutting edge 58-2, and a side wall 58-3 (see also FIG. 11) that extends between end portion 58-1 and distal cutting edge 58-2. End portion 58-1 is affixed to the cannula mount 54-3, with end portion 58-1 being in fluid communication with the proximal axial bore 54-4 of actuator body 54.

Side wall 58-3 defines an inner lumen 58-4. Inner lumen 58-4 is slidably received over the cannula support rod 44. Cannula support rod seal 56, in the form of a rubber O-ring, is positioned within proximal axial bore 54-4 of the actuator body 54. Cannula support rod 44 is received through the aperture of cannula support rod seal 56, with cannula support rod seal 56 being radially interposed between actuator body 54 and cannula support rod 44. As such, cannula support rod seal 56 is configured to be axially stationary within proximal axial bore 54-4 of actuator body 54, while being axially movable along the cannula support rod 44 with actuator body 54.

Figure 12:
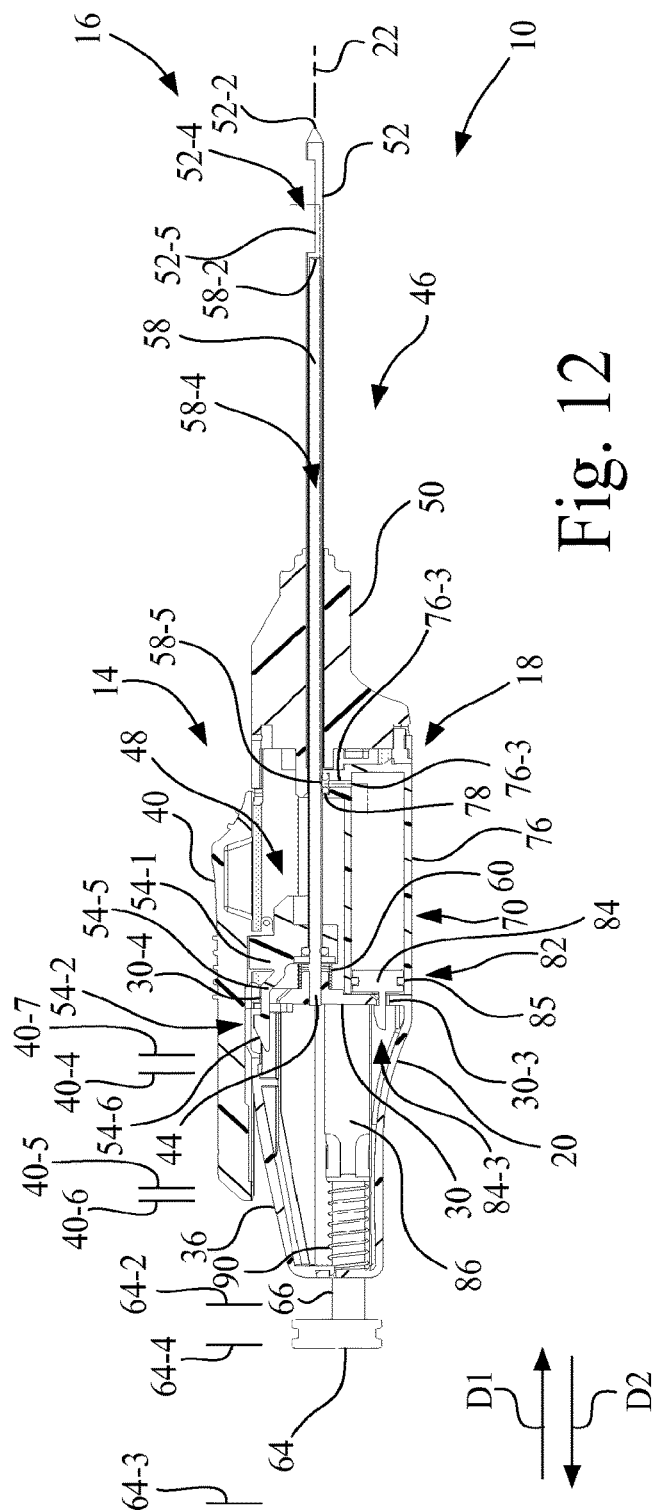
FIG. 12 is a section view corresponding to the section of FIG. 7, showing the slider body of the trigger slide assembly and the inner cannula assembly in a further retracted, vacuum application position.
Figure 13:
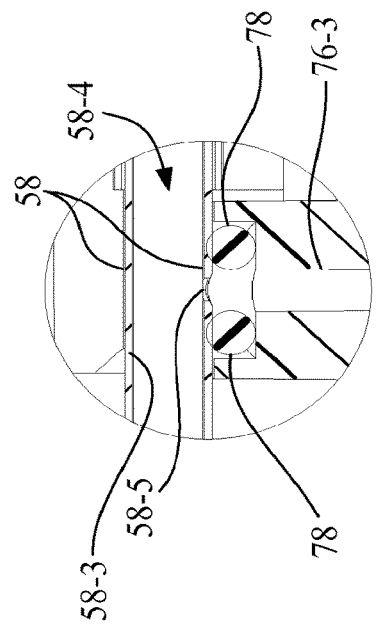
FIG. 13 is an enlarged view of a portion of the section view of FIG. 12, showing the vacuum source with the chamber vacuum port open and in fluid communication with the vacuum side port of the cutting cannula side wall.

Referring also to FIGS. 12 and 13, cutting cannula 58 further includes a vacuum side port 58-5 that extends through the side wall 58-3 at the end portion 58-1 and is in fluid communication with inner lumen 58-4. With cutting cannula 58 positioned in lumen 52-4 of outer cannula 52, vacuum side port 58-5 is further in fluid communication with a distal portion of outer cannula 52 that includes elongate side opening 52-5.

Figure 14:
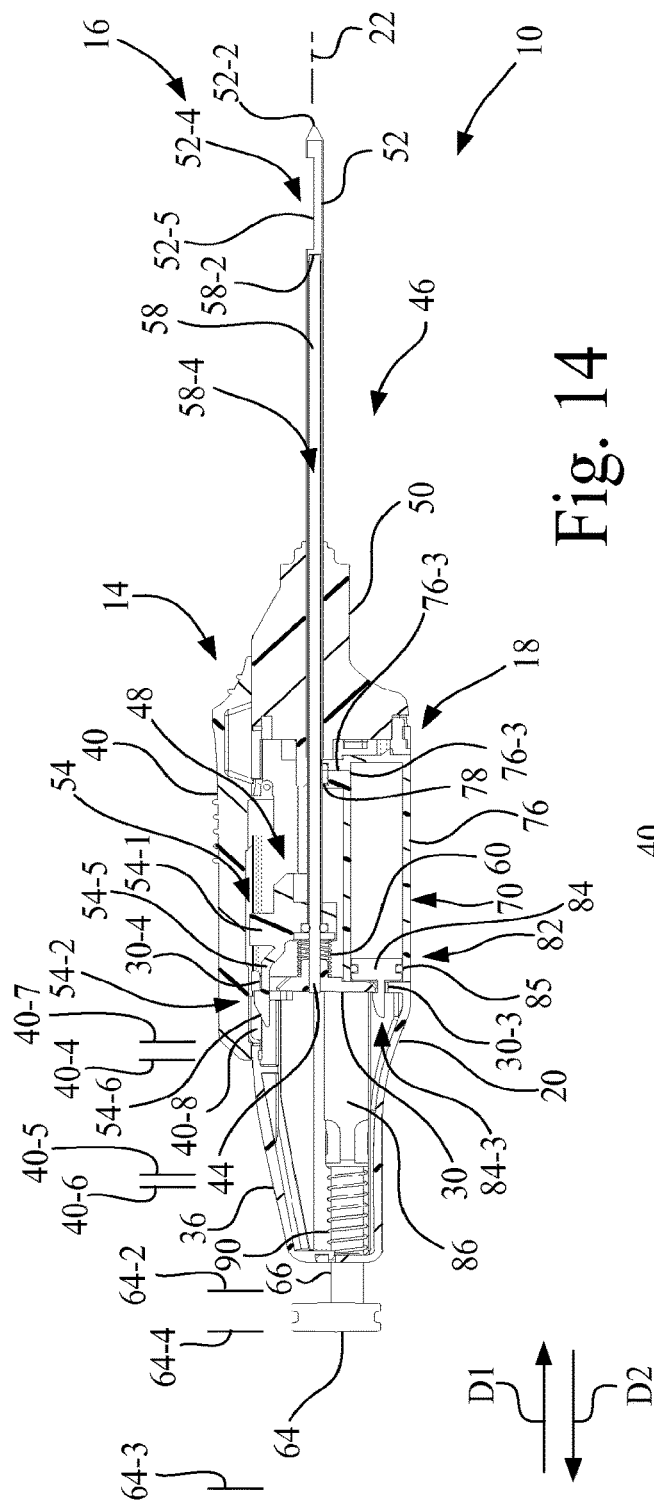
FIG. 14 is a section view corresponding to the section of FIG. 7, showing the inner cannula assembly in the primed (cocked) position, and with the slider body of the trigger slide assembly returned to the home position.

Referring again also to FIGS. 3 and 7-9, a cannula drive spring 60, e.g., in the form of a coil spring, is positioned in distal chamber 34 of housing body 20, between interior wall 30 of housing body 20 and the actuator body 54 of the inner cannula assembly 48. Referring also to FIGS. 10, 12, and 14, cannula drive spring 60 is configured to compress to store energy when the inner cannula assembly 48 is moved in the proximal direction D2 to the retracted position, at which time latch head 54-6 of proximal latch mechanism 54-2 passes through the cannula latch opening 30-4 of interior wall 30 of housing body 20 to thereby releasably latch inner cannula assembly 48 (including elongate cutting cannula 58) in a retracted position. Likewise, cannula drive spring 60 is configured to decompress to release the stored energy to propel the inner cannula assembly 48 in a distal direction D1 when proximal latch mechanism 54-2 is released from its latched state.

As best shown in FIGS. 3 and 7-9, supplemental to vacuum source 18 is a vacuum prime handle mechanism 62. Vacuum prime handle mechanism 62 is configured to prime, i.e., charge, vacuum source 18 with a supply of vacuum. Vacuum prime handle mechanism 62 includes a handle base 64 and a pair of elongate handle links 66, 68 that extend in the distal direction D1 from handle base 64. Handle base 64 may include one or more parametrical gripping ridges 64-1.

The pair of elongate handle links 66, 68 is positioned to pass through the respective pair of handle link openings 24-1, 24-2 of the proximal end wall 24 and into the proximal chamber 32. Each of the pair of elongate handle links 66, 68 has a respective longitudinal slot 66-1, 68-1. Each of the pair of elongate handle links 66, 68 also is configured to pass through a respective link opening of the piston link openings 30-1, 30-2 in the interior wall 30 of the housing body 20 to engage vacuum source 18, as will be more fully described below.

Referring again to FIGS. 3 and 6, vacuum source 18 includes a vacuum chamber housing 70 having a chamber open end 72, a chamber end wall 74, and a chamber side wall 76. Chamber side wall 76 has a perimeter 76-1 corresponding to exterior surface 70-1 defining a U-shaped area in cross-section that extends longitudinally between the chamber open end 72 and the chamber end wall 74 to define a U-shaped volume 76-2. The U-shape construction of chamber side wall 76 facilitates the ability for inner cannula assembly 48 to be moveably tucked within the same footprint as that of vacuum source 18, thereby efficiently utilizing space within biopsy device 10.

Referring also to FIGS. 8-13, chamber side wall 76 has a chamber vacuum port 76-3. Referring particularly to FIGS. 11 and 13, vacuum side port 58-5 of elongate cutting cannula 58 is configured for selective fluid engagement with chamber vacuum port 76-3 of vacuum chamber housing 70. Chamber vacuum port 76-3 is configured as an elevated protrusion of the chamber side wall 76, with the elevated protrusion having an aperture that extends through the elevated protrusion of the chamber side wall 76 to the U-shaped volume 76-2. A vacuum chamber housing seal 78, in the form of a rubber O-ring, is interposed in sealing engagement between chamber vacuum port 76-3 of vacuum chamber housing 70 and elongate cutting cannula 58. When chamber vacuum port 76-3 of vacuum chamber housing 70 and vacuum side port 58-5 of elongate cutting cannula 58 are radially aligned, vacuum chamber housing seal 78 is interposed in sealing engagement between chamber vacuum port 76-3 of vacuum chamber housing 70 and vacuum side port 58-5 of elongate cutting cannula 58 so as to facilitate the establishment of vacuum in inner lumen 58-4 of cutting cannula 58.

Figure 6:
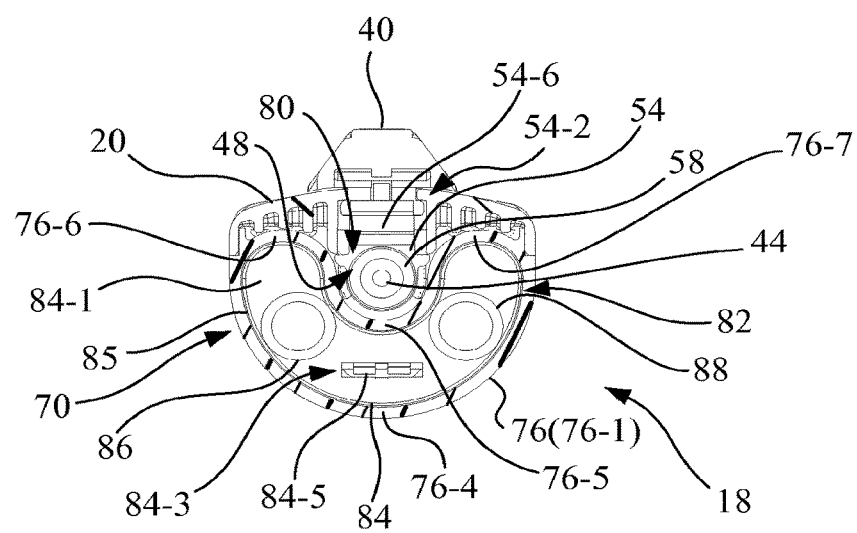
FIG. 6 is a section view of the biopsy device of FIG. 2, taken along plane 6-6.

Referring particularly to FIGS. 3 and 6, chamber side wall 76 has a first U-shaped wall section 76-4, a second U-shaped wall section 76-5, a first inverted U-shaped wall section 76-6 and a second inverted U-shaped wall section 76-7. Second U-shaped wall section 76-5 is smaller than the first U-shaped wall section 76-4 to define an upper elongate recessed trough 80 at exterior surface 70-1 at an upper portion of chamber side wall 76 of the vacuum chamber housing 70. Second U-shaped wall section 76-5 is located between the first inverted U-shaped wall section 76-6 and the second inverted U-shaped wall section 76-7 around perimeter 76-1 of the upper portion of chamber side wall 76.

As best shown in FIGS. 3 and 6, elongated recessed trough 80 is configured to receive inner cannula assembly 48, including actuator body 54 and cutting cannula 58. More particularly, actuator body 54 includes a lower curved surface that is radially supported along the longitudinal extent of recessed trough 80, and cutting cannula 58 is received in elongated recessed trough 80 without contacting chamber side wall 76. Referring again also to FIGS. 10-13, chamber vacuum port 76-3 extends outwardly from chamber side wall 76 from within elongate recessed trough 80 in a direction toward cutting cannula 58.

Referring to FIGS. 2, 3, 6, and 7, vacuum source 18 further includes a vacuum plunger mechanism 82. Vacuum plunger mechanism 82 includes a U-shaped piston 84 positioned in U-shaped volume 76-2. U-shaped piston 84 has a proximal surface 84-1 and a distal surface 84-2. A chamber seal 85, in the form of a U-shaped rubber O-ring, is configured for sealing engagement between an interior surface 76-8 of the chamber side wall 76 and the U-shaped piston 84.

Referring to FIGS. 2 and 5-10, a piston latch mechanism 84-3 extends in the proximal direction D2 from proximal surface 84-1, and is in the form of a cantilever arm 84-4 having at its free end a latch head 84-5. Together, piston latch mechanism 84-3 of U-shaped piston 84 and piston latch opening 30-3 of interior wall 30 of housing body 20 form a snap featured detent.

Figure 8:
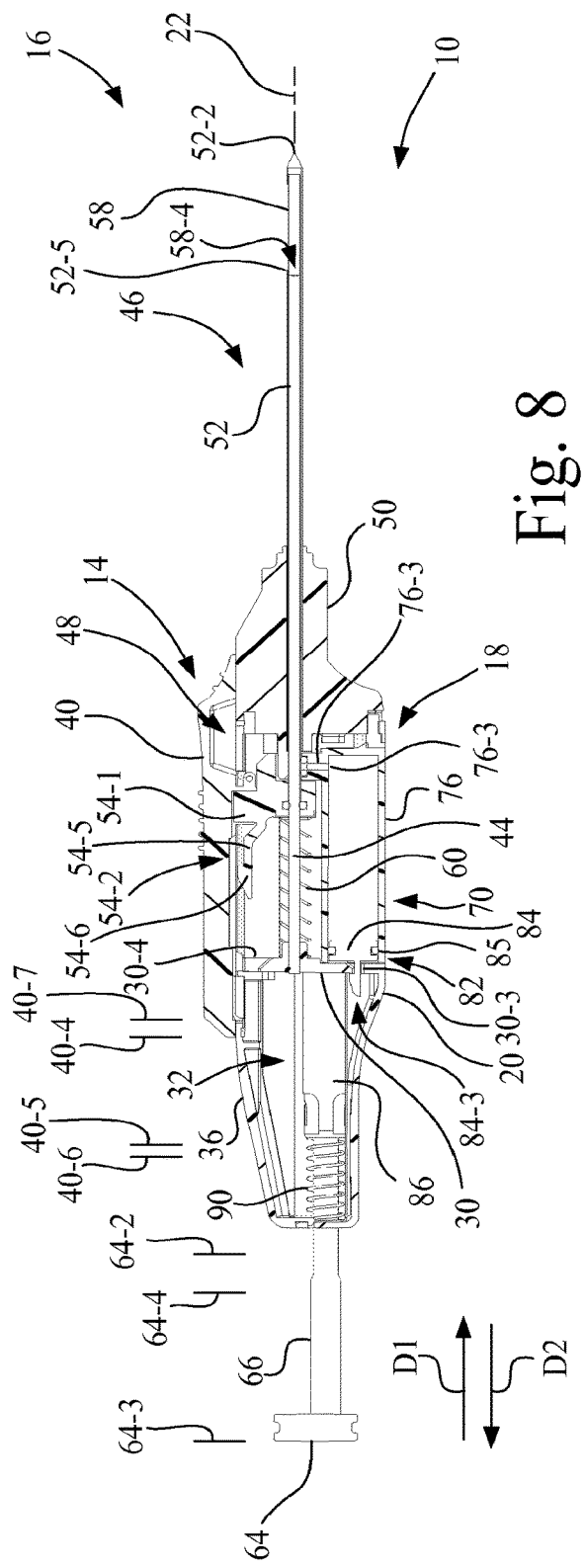
FIG. 8 is a section view corresponding to the section of FIG. 7, showing the vacuum source in the primed position and the vacuum prime handle mechanism fully retracted.
Figure 9:
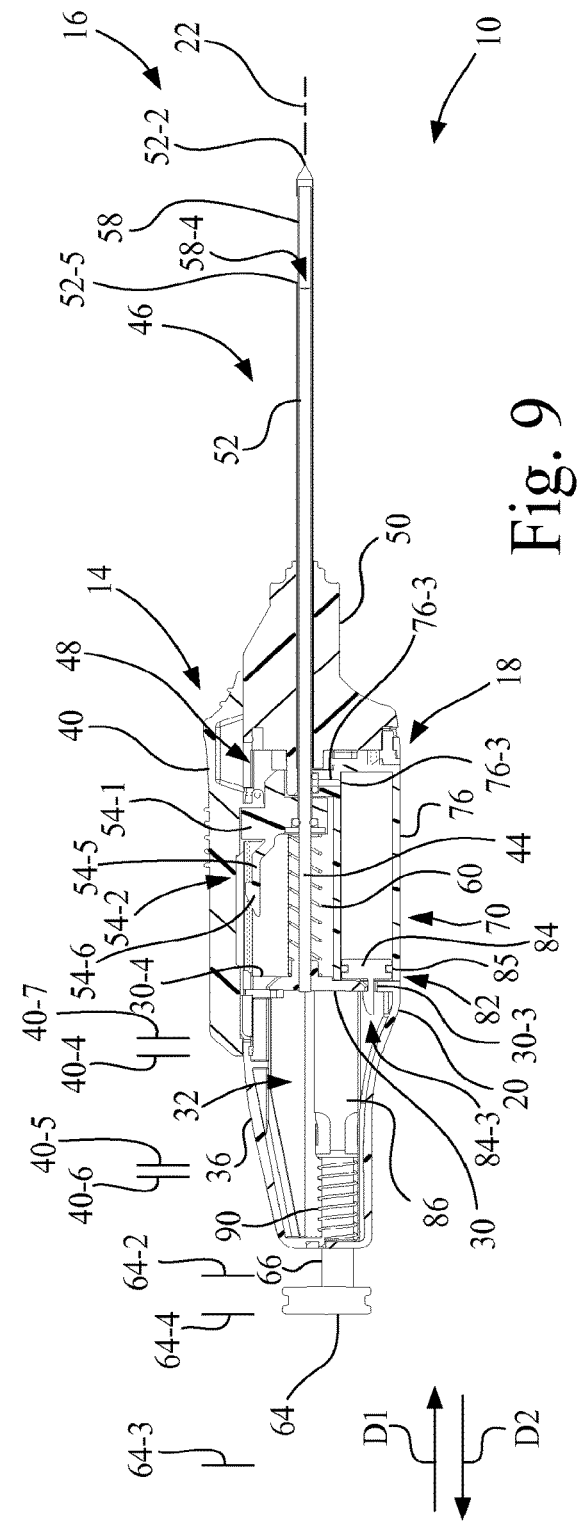
FIG. 9 is a section view corresponding to the section of FIG. 7, showing the vacuum source in the primed position and the vacuum prime handle mechanism in the return primed position.

Referring particularly to FIGS. 8 and 9, when U-shaped piston 84 is moved, i.e., retracted, in the proximal direction D2 to prime vacuum source 18, vacuum is accumulated in vacuum chamber housing 70 and thus vacuum chamber housing 70 is considered to be primed. Piston latch mechanism 84-3 is configured to pass through the piston latch opening 30-3 of interior wall 30 of housing body 20 to thereby releasably latch U-shaped piston 84 in a retracted (primed) position. More particularly, piston latch mechanism 84-3 latch head 84-5 is configured to catch a portion of interior wall 30 adjacent piston latch opening 30-3 in proximal chamber 32 to releasably latch U-shaped piston 84 in the retracted (primed) position.

Referring to FIGS. 8-10, 12 and 14, when vacuum source 18 is primed, vacuum chamber housing 70 in conjunction with U-shaped piston 84 define approximately 20 cubic centimeters of vacuum storage, and with vacuum pressure at full charge in the range of −5.0 psi to −6.0 psi (−34.4 k Pa to −41.4 k Pa).

Referring again to FIG. 3, vacuum source 18 is configured with a check valve 89 to allow vacuum to accumulate in vacuum chamber housing 70 on retraction of U-shaped piston 84 in the proximal direction D2, but also to equalize pressure when U-shaped piston 84 is released and moved in the distal direction D1 toward chamber end wall 74 in preparation for a vacuum re-prime operation. Check valve 89 is configured to facilitate fluid flow in only one direction, and may be, for example, in the form of a ball/spring valve. As shown in FIG. 3, check valve 89 is located on chamber end wall 74 of vacuum chamber housing 70. Alternatively, it is contemplated that check valve 89 may be built into U-shaped piston 84.

Referring to FIGS. 3, 5, 6, 8-10, 12 and 14, a pair of piston link rods 86, 88 extends proximally from proximal surface 84-1 of the U-shaped piston 84. Each of the pair of piston link rods 86, 88 has a respective proximal end 86-1, 88-1 and a bore 86-2, 88-2 extending distally from the proximal end

86-1, 88-1. Each of the pair of piston link rods 86, 88 is configured to pass through a respective piston link opening 30-1, 30-2 (see FIGS. 4 and 5) in interior wall 30 of housing body 20 and into proximal chamber 32 (see FIGS. 8-10). Each of a pair of bias springs 90, 92 is respectively received over the pair of elongate handle links 66, 68, and is positioned between the proximal end wall 24 of the housing body 20 and a respective proximal end 86-1, 88-1 of the pair of piston link rods 86, 88. A pair of joining features 86-3, 88-3, e.g., tabs, clips, pins, etc., may be affixed to, or integral with, a respective piston link rod of the pair of piston link rods 86, 88 of vacuum plunger mechanism 82 and is configured to be slidably engaged within a respective longitudinal slot 66-1, 68-1 of a respective elongate handle link 66, 68 of vacuum prime handle mechanism 62. In the present embodiment, each of the pair of joining features 86-3, 88-3 is formed as a part of a snap tab located on a respective piston link rod of the pair of piston link rods 86, 88 and is configured to engage a respective longitudinal slot 66-1, 68-1 of a respective elongate handle link 66, 68 of vacuum prime handle mechanism 62. Alternatively, it is contemplated that joining features 86-3, 88-3 may be a separate fastener, e.g., a pin.

The operation of biopsy device 10 now will be described with primary reference to FIGS. 7-15, and with overall reference to FIG. 3.

FIG. 7 shows biopsy device 10 with all components in their respective home position. More particularly, the home position 40-4 of slider body 40 is the position to which slider body 40 will always return when no external force is applied to slider body 40. Also, a home position 64-2 of handle base 64 of vacuum prime handle mechanism 62 is the position where handle base 64 is immediately adjacent to the proximal-most portion of housing body 20.

Referring to FIG. 8, to ready biopsy device 10 for performing a biopsy procedure, vacuum source 18 is primed, i.e., vacuum is stored in vacuum chamber housing 70. To prime vacuum source 18, the user pulls handle base 64 in the proximal direction D2 to its proximal-most position 64-3, which in turn causes a proximal retraction in the proximal direction D2 of vacuum plunger mechanism 82 to a fully retracted (prime) position.

More particularly, a proximal movement of handle base 64 toward proximal-most position 64-3 results in a proximal movement of the handle links 66, 68. Since handle links 66, 68 are slidably coupled to piston link rods 86, 88, the proximal movement of handle links 66, 68 result in a proximal movement of vacuum plunger mechanism 82 to the vacuum primed position, wherein when handle base 64 reaches proximal-most position 64-3, piston latch mechanism 84-3 passes through the piston latch opening 30-3 of interior wall 30 of housing body 20 and releasably latches U-shaped piston 84 in a retracted (primed) position. Simultaneously, springs 90, 92 are compressed.

Referring to FIG. 9, after priming vacuum source 18, handle base 64 is moved in the distal direction D1 to the proximal intermediate position 64-4. Because handle links 66, 68 are fixedly attached to handle base 64, the movement of handle base 64 also results in movement of handle links 66, 68. However, since handle links 66, 68 are slidably joined to piston link rods 86, 88 via longitudinal slot 66-1, 68-1, and while U-shaped piston 84 is latched in a retracted (primed) position, handle links 66, 68 are free to move in the distal direction D1 within piston link rods 86, 88 until handle links 66, 68 are collapsed into piston link rods 86, 88 to a point of resistance. The point of resistance may be defined, for example, by the length of longitudinal slots 66-1, 68-1, or alternatively, when the distal end of handle links 66, 68 encounter the proximal surface 84-1 of U-shaped piston 84 within piston link rods 86, 88.

Thus, with handle base 64 at proximal intermediate position 64-4, distal movement of handle base 64 is restricted. However, if it is desired to re-prime and/or de-prime vacuum source 18, the user may do so by firmly applying pressure (e.g., a firm bump with the hand) in the distal direction D1 to handle base 64 to overcome the latch force of piston latch mechanism 84-3, and with springs 90, 92 decompressing, U-shaped piston 84 is moved back to its home position (see FIG. 7).

After priming vacuum source 18 (FIG. 9), biopsy device 10 is ready for insertion of cannula assembly 16 into the tissue of the patient for positioning at the biopsy site. In particular, cannula assembly 16 is inserted into the patient such that elongate side opening 52-5 of outer cannula 52 is positioned adjacent the tissue to be sampled at the biopsy site.

Referring to FIGS. 10, 12 and 14, next slider body 40 of trigger slide assembly 14 will be moved sequentially from home position 40-4 to first proximal position 40-5 (FIG. 10), then to second proximal position 40-6 (FIG. 12), then back to home position 40-4 (FIG. 9), and then to distal-most position 40-7 (see FIG. 14), to effect a tissue sample capture sequence.

Again, home position 40-4 (see, e.g., FIG. 9) of slider body 40 is the position to which slider body 40 will always return when no external force is applied to slider body 40. Thus, if at any time slider body 40 is released by the user, either intentionally or inadvertently, slider body 40 will always return to the home position 40-4 and the sequence can be resumed from home position 40-4.

Referring to FIG. 10, first proximal position 40-5 is the position of slider body 40 where a prime (cocking) of inner cannula assembly 48, including cutting cannula 58, occurs. As slider body 40 is moved in the proximal direction D2, slider body 40 engages drive tab 54-1 of actuator body 54 of inner cannula assembly 48 to which cutting cannula 58 is fixedly attached. Thus, a longitudinal movement of slider body 40 in the proximal direction D2 will result in a corresponding movement is proximal direction D2 of inner cannula assembly 48 having cutting cannula 58.

This proximal movement of the slider body to first proximal position 40-5 retracts the inner cannula assembly 48 a first distance to latch the proximal latch mechanism 54-2 of the elongate cutting cannula 58 in a retracted (primed, or cocked) position and compresses the cannula drive spring 60. More particularly, proximal latch mechanism 54-2 passes through the cannula latch opening 30-4 of interior wall 30 of housing body 20 to releasably latch the elongate cutting cannula 58 in the retracted (primed, or cocked) position. In the primed (cocked) position, elongate cutting cannula 58 has been retracted to open elongate side opening 52-5 of outer cannula 52.

Referring also to FIG. 11, when slider body 40 of trigger slide assembly 14 is in any position other than in the second proximal position 40-6, cutting cannula 58 will block chamber vacuum port 76-3 of vacuum chamber housing 70, and thus prevent the supply of vacuum stored in vacuum chamber housing 70 from escaping.

Thus, referring now to FIG. 12, in order to apply vacuum to elongate side opening 52-5 of outer cannula 52 during the biopsy procedure, slider body 40 is moved to the second proximal position 40-6, which is spaced a distance more proximal than first proximal position 40-5. Thus, the second proximal movement of the slider body to second proximal position 40-6 retracts the inner cannula assembly 48 a second distance cumulative with the first proximal distance associated with first proximal position 40-5, so as to radially align vacuum side port 58-5 of elongate cutting cannula 58 with the chamber vacuum port 76-3 of the vacuum source 18 (see FIG. 13) such that vacuum is transferred from vacuum chamber housing 70 of vacuum source 18 to the inner lumen 58-4 of cutting cannula 58, and in turn to elongate side opening 52-5 of outer cannula 52, so as to apply vacuum to the tissue adjacent elongate side opening 52-5 so as to draw the tissue into elongate side opening 52-5 prior to releasing cutting cannula 58.

The user will maintain slider body 40 of trigger slide assembly 14 at the second proximal position 40-6 only so long as deemed necessary to establish the vacuum at elongate side opening 52-5 of outer cannula 52 and draw the tissue to be sampled into elongate side opening 52-5 of outer cannula 52. This time period may be, for example, from 0.5 to 2 seconds, as determined by the practitioner. The user will then release slider body 40, and biasing spring 42 will return slider body 40 to home position 40-4.

Figure 15:
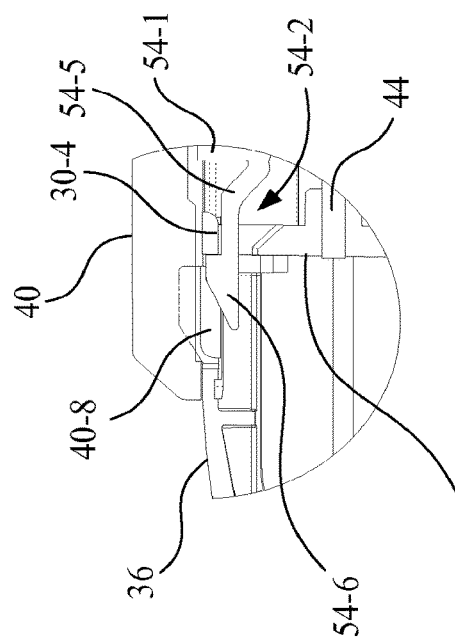
FIG. 15 is an enlarged view of a portion of the section view of FIG. 14, showing the slider body of the trigger slide assembly ready to deflect the cannula latch mechanism downwardly for release upon a distal movement of the slider body beyond its home position.

Referring to FIGS. 14 and 15, distal-most position 40-7 of slider body 40 is a position distal to home position 40-4, and is the position where a firing (de-priming) of inner cannula assembly 48, including cutting cannula 58, has occurred, i.e., to sever a tissue sample received into elongate side opening 52-5 of outer cannula 52. As shown in FIGS. 14 and 15, slider body 40 includes a depression feature 40-8 configured such that when slider body 40 is moved distally from home position 40-4 toward distal-most position 40-7, depression feature 40-8 engages latch head 54-6 of proximal latch mechanism 54-2 of inner cannula assembly 48 and forces latch head 54-6 of proximal latch mechanism 54-2 downwardly to release distal contact of latch head 54-6 with interior wall 30 at cannula latch opening 30-4. As such, cannula drive spring 60 is released (i.e., fired, or de-primed; see FIG. 7) from the compressed state to propel inner cannula assembly 48, including cutting cannula 58, in the distal direction D1, such that distal cutting edge 58-2 of cutting cannula travels past elongate side opening 52-5 of outer cannula 52 to sever a tissue sample previously received into elongate side opening 52-5 of outer cannula 52 and capture the tissue sample within cannula assembly 16.

As this time, cannula assembly 16 of biopsy device 10 is removed from the patient. The inner cannula assembly 48 having cutting cannula 58 is then retracted to remove the captured tissue sample from elongate side opening 52-5 of outer cannula 52.

If a further sample from this same patient is desired, then the process described above may be repeated.

Following acquisition of all desired samples from the patient, it is recommended that biopsy device 10 be disposed of in its entirety in a safe manner.

While this invention has been described with respect to at least one embodiment, those skilled in the art will recognize that the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device, comprising:
a housing body defining a longitudinal axis;
a cannula assembly having a first elongate cannula having a first side wall configured to define a first lumen and an elongate side opening that extends through the first side wall, and a second elongate cannula coaxial with the first elongate cannula, the second elongate cannula having a second side wall configured to define a second lumen and a cutting edge, the second side wall having a vacuum side port in fluid communication with the second lumen;
a vacuum source positioned in the housing body, the vacuum source having a chamber side wall having a chamber vacuum port, the vacuum source having a seal interposed in sealing engagement between the chamber vacuum port and the second elongate cannula; and
a trigger slide assembly coupled to the housing body, and coupled to the cannula assembly, and configured to move the second elongate cannula to align the vacuum side port of the second elongate cannula with the chamber vacuum port of the vacuum source to supply vacuum from the vacuum source to the second lumen of the second elongate cannula;
wherein the vacuum source comprises a vacuum chamber housing having a chamber open end, a chamber end wall, and the chamber side wall, the chamber side wall having a perimeter that defines an elongate recessed trough having a longitudinal extent, and wherein the second elongate cannula is positioned within the elongate recessed trough without contacting the chamber side wall.

2. The biopsy device of claim 1, wherein the chamber side wall has a perimeter defining a U-shaped area in cross-section that extends longitudinally between the chamber open end and the chamber end wall to define a U-shaped volume.

3. The biopsy device of claim 2, comprising:
a vacuum plunger mechanism having a U-shaped piston that is positioned in the U-shaped volume of the vacuum chamber housing; and
a chamber seal configured for sealing engagement between an interior surface of the chamber side wall and the U-shaped piston.

4. The biopsy device of claim 3, wherein:
the housing body includes an interior wall having a piston latch opening; and
the vacuum plunger mechanism includes a piston latch mechanism that extends from a proximal surface of the U-shaped piston, the piston latch mechanism configured to pass through the piston latch opening of the interior wall and releasably latch the U-shaped piston in a retracted position when the U-shaped piston is moved in a proximal direction.

5. The biopsy device of claim 4, wherein:
the interior wall of the housing body has a pair of link openings; and
the U-shaped piston includes a pair of piston link rods that extend proximally from the proximal surface of the U-shaped piston, each of the pair of piston link rods having a proximal end and a bore extending distally from the proximal end, and the pair of piston link rods configured to pass through the corresponding pair of link openings in the interior wall of the housing body, and further comprising:
a vacuum prime handle mechanism having a handle base and a pair of elongate handle links that extend from the handle base, each of the pair of elongate handle links having a longitudinal slot, the pair of elongate handle links being slidably received into the bores of the pair of piston link rods; and
a pair of joining features configured to connect the pair of piston link rods with the pair of elongate handle links in sliding engagement.

6. The biopsy device of claim 1, wherein the chamber vacuum port extends outwardly from the chamber side wall from within the elongate recessed trough and in a direction toward the second elongate cannula.

7. The biopsy device of claim 1, wherein the second elongate cannula is positioned within the first lumen of the first elongate cannula, the first elongate cannula being stationary with respect to the housing body, and the second elongate cannula being movable within the first lumen relative to the housing body, the second lumen of the second elongate cannula being in fluid communication with the first lumen of the first elongate cannula.

8. The biopsy device of claim 1, comprising a cannula support rod affixed to the housing body, and being coaxial with the first elongate cannula and the second elongate cannula, the cannula support rod being received in the second lumen of the second elongate cannula.

9. A biopsy device, comprising:
a housing body defining a longitudinal axis;
a first cannula assembly having a first elongate cannula that extends along the longitudinal axis, the first elongate cannula having a first side wall configured to define a first lumen and having an elongate side opening that extends through the first side wall;
a second cannula assembly including a second cannula body coupled to a second elongate cannula that is slidably received in the first lumen of the first elongate cannula,
the second cannula body having a drive tab and a proximal latch mechanism configured to releasably latch the second elongate cannula in a retracted position,
the second elongate cannula having a second side wall having a second lumen, and having a vacuum side port that extends through the second side wall and is in fluid communication with the second lumen, and
a cannula drive spring configured to compress when the proximal latch mechanism is moved to the retracted position and configured to decompress to propel the second cannula assembly in a distal direction when the proximal latch mechanism is released from the retracted position;
a vacuum source positioned in the housing body, the vacuum source configured to store a vacuum, the vacuum source including a chamber side wall defining a volume, the chamber side wall having a chamber vacuum port, and having a vacuum seal interposed in sealing engagement between the chamber vacuum port and the second elongate cannula; and
a trigger slide assembly having a slider body coupled to the housing body and coupled to the drive tab of the second cannula body, and configured such that:
a first proximal movement of the slider body in a proximal direction retracts the second cannula assembly a first distance to latch the proximal latch mechanism of the second cannula assembly in the retracted position and compress the cannula drive spring;
a second proximal movement of the slider body in the proximal direction retracts the second cannula assembly a second distance cumulative with the first distance to radially align the vacuum side port of the second elongate cannula with the chamber vacuum port of the vacuum source to supply the vacuum from the vacuum source to the second lumen of the second elongate cannula; and
a third movement of the slider body releases the proximal latch mechanism such that the cannula drive spring decompresses to propel the second elongate cannula of the second cannula assembly in the distal direction.

10. The biopsy device of claim 9, wherein the third movement of the slider body is in the distal direction opposite the proximal direction.

11. The biopsy device of claim 9, wherein the chamber side wall defines a U-shaped volume, wherein a portion of the chamber side wall defines an elongate recessed trough having a longitudinal extent, and wherein the second elongate cannula is positioned within the elongate recessed trough external to the chamber side wall and without contacting the chamber side wall.

12. The biopsy device of claim 9, wherein the chamber side wall of the vacuum source has a perimeter defining a U-shaped area in cross-section that extends longitudinally to define a U-shaped volume, and comprising a vacuum plunger mechanism having a U-shaped piston that is positioned in the U-shaped volume, and a chamber seal configured for sealing engagement between an interior surface of the chamber side wall and the U-shaped piston.

13. The biopsy device of claim 12, wherein:
the housing body includes an interior wall having a piston latch opening; and
the vacuum plunger mechanism includes a piston latch mechanism that extends from a proximal surface of the U-shaped piston, the piston latch mechanism configured to pass through the piston latch opening of the interior wall and releasably latch the U-shaped piston in a retracted position when the U-shaped piston is moved in the proximal direction to the retracted position.

14. The biopsy device of claim 13, comprising:
a pair of piston link rods that extend proximally from the proximal surface of the U-shaped piston, each of the pair of piston link rods having a proximal end and a bore extending distally from the proximal end;
a vacuum prime handle mechanism having a handle base and a pair of elongate handle links that extend from the handle base; and
a pair of joining features configured to connect the pair of piston link rods to the pair of elongate handle links in sliding engagement.

15. The biopsy device of claim 9, wherein the chamber side wall has a perimeter that defines an elongate recessed trough having a longitudinal extent, and wherein the second elongate cannula is positioned within the elongate recessed trough external to the chamber side wall and without contacting the chamber side wall.

16. The biopsy device of claim 15, wherein the chamber vacuum port extends outwardly from the chamber side wall from within the elongate recessed trough and in a direction toward the second elongate cannula.

17. The biopsy device of claim 16, wherein the first elongate cannula is stationary with respect to the housing body, and the second elongate cannula is movable within the first lumen relative to the housing body, the second lumen of the second elongate cannula being in fluid communication with the elongate side opening of the first elongate cannula.

18. The biopsy device of claim 9, comprising a cannula support rod affixed to the housing body, and being coaxial with the first elongate cannula and the second elongate cannula, the cannula support rod being received in the second lumen of the second elongate cannula.

19. The biopsy device of claim 9, wherein the chamber side wall has a perimeter defining a U-shaped area in cross-section, and the chamber side wall extends longitudinally between a chamber open end and a chamber end wall of the vacuum source to define a U-shaped volume.

* * * * *

UNITED STATES PATENT AND TRADEMARK OFFICE
CERTIFICATE OF CORRECTION

| | | |
|---|---|---|
| PATENT NO. | : 11,534,148 B2 | Page 1 of 1 |
| APPLICATION NO. | : 16/570097 | |
| DATED | : December 27, 2022 | |
| INVENTOR(S) | : Rory M. Schlarb and Chad C. Van Liere | |

It is certified that error appears in the above-identified patent and that said Letters Patent is hereby corrected as shown below:

On the Title Page

In page 4, Column 1, Item (56), U.S. patent documents, cite no 101 delete "3,002,713" and insert --8,002,713--, therefor.

In page 4, Column 1, Item (56), U.S. patent documents, cite no 101 delete "A1" and insert --B2--, therefor.

In page 4, Column 1, Item (56), U.S. patent documents, cite no 102 delete "3,012,102" and insert --8,012,102--, therefor.

In page 4, Column 1, Item (56), U.S. patent documents, cite no 102 delete "A1" and insert --B2--, therefor.

Signed and Sealed this
Twenty-first Day of February, 2023

*Katherine Kelly Vidal*

Katherine Kelly Vidal
*Director of the United States Patent and Trademark Office*